(12) United States Patent
Yakymyshyn et al.

(10) Patent No.: US 7,845,847 B2
(45) Date of Patent: Dec. 7, 2010

(54) TEMPERATURE SENSOR AND EXTENSOMETER FOR ELECTRICAL POWER CABLES

(75) Inventors: Christopher Yakymyshyn, Seminole, FL (US); Michael Allen Brubaker, Loveland, CO (US); Pamela Jane Hamilton, Seminole, FL (US)

(73) Assignee: FieldMetrics, Inc., Seminole, FL (US)

( * ) Notice: Subject to any disclaimer, the term of this patent is extended or adjusted under 35 U.S.C. 154(b) by 25 days.

(21) Appl. No.: 12/501,510

(22) Filed: Jul. 13, 2009

(65) Prior Publication Data

US 2009/0279581 A1 Nov. 12, 2009

Related U.S. Application Data

(62) Division of application No. 11/164,131, filed on Nov. 10, 2005, now Pat. No. 7,575,371.

(60) Provisional application No. 60/522,833, filed on Nov. 11, 2004.

(51) Int. Cl.
*G01K 11/24* (2006.01)
*G01B 17/00* (2006.01)
*G01S 15/00* (2006.01)
*G01N 29/00* (2006.01)
*G01V 1/00* (2006.01)
*G01H 5/00* (2006.01)

(52) U.S. Cl. .......... 374/119; 374/141; 374/117; 374/45; 374/55; 374/6; 702/130; 702/159; 367/127; 367/129; 367/99; 73/1.81; 73/1.82; 73/628; 73/597; 73/632

(58) Field of Classification Search ......... 374/141, 374/119, 117, 45, 6, 55; 702/130, 159; 367/127, 367/129, 99; 73/1.81, 1.82, 628, 597, 632
See application file for complete search history.

(56) References Cited

U.S. PATENT DOCUMENTS 4,035,762 A * 7/1977 Chamuel .............. 367/117
5,044,769 A * 9/1991 Kulczyk et al. ......... 374/119

\* cited by examiner

*Primary Examiner*—Lisa M Caputo
*Assistant Examiner*—Mirellys Jagan

(57) ABSTRACT

A thermometer and extensometer for cables and conductors is described. The travel time of one or more acoustic signals along a conductor is used to determine the temperature along the conductor and the length of the conductor. The acoustic frequency is selected to minimize temporal dispersion of the propagating acoustic energy. The technique can be used to measure the temperature of the windings in a transformer or other electrical apparatus.

12 Claims, 9 Drawing Sheets

TEMPERATURE SENSOR AND EXTENSOMETER FOR ELECTRICAL POWER CABLES

CROSS REFERENCE TO PRIOR APPLICATION

This application is a divisional of U.S. application Ser. No. 11/164,131 filed Nov. 10, 2005 and entitled "Temperature Sensor and Extensometer," which claims the priority of U.S. Provisional Application Ser. No. 60/522,833 filed Nov. 11, 2004 and entitled "Temperature Sensor and Extensometer", the subject matter of which is incorporated herein by reference.

FIELD OF THE INVENTION

The present invention relates to measuring the temperature of a long conductor embedded in an electrical power apparatus, and to measuring the change in length of a long conductor embedded in an electrical power apparatus.

DESCRIPTION OF THE PRIOR ART

Often it is desirable to measure the temperature of an internal region of a long, cylindrical object. For example, electrically conductive wires used in power transmission and distribution systems operate at high temperatures when carrying large currents. Examples of these cables include stranded copper, all-aluminum (AAC), steel-reinforced aluminum (ACSR), and steel-supported aluminum (ACSS). The thermal expansion of the conductor causes the conductor length to increase, resulting in undesirable physical sag when it is supported on its two ends by towers or poles. In aircraft or automotive wiring, current can cause localized heating of electrical conductors when they are bundled in such a way as to reduce thermal transport of heat away from the heated region. The localized heating can lead to failure of the dielectric insulation on the wire. In power transformers and underground or undersea power cables, the temperature rise of the conductor can cause thermal breakdown or aging of the electrically insulating medium surrounding the conductor. The local temperature of the conductor needs to be known in real-time to avoid this occurrence.

Several methods have been disclosed to measure the sag of an overhead power line. None of the prior art relies on acoustic measurements of the conductor. For example, a video camera has been used to monitor the position of a target mounted to the predicted maximum sag point of the conductor. A wireless transponder mounted at the predicted maximum sag point has also been used to measure the conductor height using a Global Positioning System receiver with differential measurement accuracy enhancement.

The temperature of an overhead conductor has been predicted based on information about the line current, and current weather conditions at the conductor location. Other temperature measurement techniques have used optical fibers for distributed temperature sensing, thermocouples for point measurements on the surface of the conductor, and thermal imaging or temperature measurement cameras to calculate the conductor surface temperature based on thermal emissivity of the conductor.

The temperature measurement of an underground cable has been disclosed using a distributed optical fiber sensor, or by measuring the current in the cable and calculating the cable temperature based on the cable's thermal properties, and the thermal properties and temperature of the environment surrounding the cable.

Measuring the temperature of the conductor windings inside a power transformer is a difficult problem. Disclosed techniques have included measuring the temperature of the insulating oil flowing through the windings, and calculating the winding temperature based on hydrodynamic and thermal models of the transformer structure; measuring the temperature at discrete points in the winding with optical temperature sensors; and calculating the winding temperature based on the thermal properties of the transformer structure, the ambient weather conditions and the current flowing through the transformer windings.

In the above-mentioned prior art, acoustic or ultrasonic sensors were not employed to perform the temperature or sag measurements. These methods also suffer from high cost, difficulty in retrofitting to installed equipment, or difficulty in generating accurate models of installed equipment for calculation purposes due to changes in material properties over time (for example, the emissivity of an overhead conductor changes with weather conditions and age, resulting in large errors in temperature measurements collected using thermal imaging).

Acoustic techniques have been disclosed to measure other properties of conductors, cables, pipes or rods. In U.S. Pat. No. 6,382,029, issued May 7, 2002, Shoureshi et al. disclose the use of an Electro-Magnetic Acoustic Transducer (EMAT) to generate and detect acoustic waves on an overhead conductor. The detected acoustic signals are processed using a combination of neural networks and fuzzy logic to identify damaged regions along the cable. A similar invention disclosed by Kwun et al. in U.S. Pat. No. 5,456,113, issued Oct. 10, 1995 employed an EMAT to induce acoustic waves in a ferromagnetic cable or rope to measure defects therein. An acoustic method to measure the length of a large bolt was disclosed by Jones in U.S. Pat. No. 4,413,518 issued on Nov. 8, 1983. A similar method was disclosed by McFaul et al. in U.S. Pat. No. 3,759,090 issued in Sep. 18, 1973, and by Pagano in U.S. Pat. No. 3,969,810 issued on Jul. 20, 1976. An acoustic pulse was introduced into one end of the bolt, and the acoustic wave reflected from the opposite end of the bolt was detected and used to calculate the length of the bolt. The temperature of the bolt was not measured, but rather it was treated as an operator-defined parameter. Smith et al. disclosed in U.S. Pat. No. 6,923,065 issued Aug. 2, 2005, and Smith discloses in U.S. Pat. No. 6,662,660 issued Dec. 16, 2003, the use of acoustic time of flight along an Aramid fiber rope found in elevators to determine the Young's modulus of the fibers and the remaining strength of the rope. Newman disclosed in U.S. Pat. No. 4,584,676 issued on Apr. 22, 1986 and Kayem et al. disclosed in U.S. Pat. No. 4,241,430 issued Dec. 23, 1980, the use of acoustic transducers to launch an acoustic wave into a pipe. The acoustic wave was guided down the pipe length, reflected partially at the end of the pipe, and detected at the launch end of the pipe. The time delay was used to calculate the length of the pipe.

A method of measuring the conductor temperature when the conductor is an overhead power line, a spiral winding in a transformer, or confined inside of a solid or liquid dielectric in an underground cable, would be beneficial, especially if the method permitted direct, non-invasive measurements of the conductor temperature. For the case when an overhead conductor is being monitored, the length of the conductor between support towers can also be measured to calculate the conductor sag.

BRIEF DESCRIPTION OF THE PRESENT INVENTION

The invention disclosed herein relies on the method of acoustic thermometry to measure the temperature and/or the length of a solid or a stranded electrical conductor. By launching an acoustic tone burst along the conductor, the travel time to a distant receiver location (which may be several miles away) or the round-trip travel time between the launch location and a partially reflective object can be accurately measured. The transit time depends on the square root of the temperature-dependent elastic (Young's) modulus of the cable. Since the Young's moduli of metals have known temperature dependences, the transit time provides a measure of the average temperature along the travel path. The acoustic frequency and mode structure can be adjusted to ensure that the acoustic mode is distributed uniformly through the cable cross-section, providing a temperature measurement of the conductor's interior. The conductor may be an overhead power line, a winding inside of a power transformer or the central conductor of an underground, electrically shielded power cable.

By simultaneously introducing a second acoustic pulse at a second central frequency that differs from the central frequency of the first acoustic pulse, the two detected acoustic signals will travel at different velocities. The two measured time delays can be used to calculate both the temperature of the conductor and the length of the conductor. The length of the conductor can then be used to determine the amount of sag that an overhead conductor is experiencing.

Time domain reflectometry can also be used to infer more localized temperature measurements. For example, an overhead line is clamped at periodic intervals (at each tower support location), and it is expected that a small acoustic reflection will be generated at each clamp point. The transit time of the individual reflection signals can be used to measure the average temperature along each span. Additional clamps can be installed near regions of interest, if desired.

When applied to transformer windings, acoustic reflections will occur at each bend (or transposition of the bundled conductors comprising the turns) in the winding. This creates an acoustic reflection from each bend, each of which will have a slightly different travel time. By calculating the difference in arrival times of adjacent reflections, the temperature of the conductor between successive bends can be calculated. This permits the temperature profile of the transformer winding to be measured.

For underground cables, an acoustic signal can be launched at one end of the cable. Reflections from cable perturbations such as defects or bends can be used to calculate the average temperature of the conductor between successive cable perturbations.

An operating sensor system for an overhead power line would have transducers and associated support electronics enclosed in a pod and clamped to the conductor at periodic locations. The spacing would be on the order of 0.01-100 kilometers, permitting a few pods to access the temperature distribution along a substantial length of conductor. The pod itself provides power for the electronics and transducers, data acquisition and processing, wireless transmission to control centers, and diagnostic capabilities.

An operating system for a transformer winding would have a pod attached to one end of the primary or secondary winding. The pod would launch acoustic signals down the conductor and measure any acoustic reflections returning as a function of time. Alternatively, a second pod could be attached to the neutral bushing to receive signals.

An operating system for an underground or undersea cable would have a pod attached to one end of the cable. The pod would launch acoustic signals down the cable's center conductor and monitor any acoustic reflections returning as a function of time.

In addition to transient thermal effects on the Young's modulus, permanent annealing effects have been observed in all-aluminum (AAC) or steel-reinforced aluminum (ACSR) overhead conductors due to excessive mechanical loading or extreme thermal excursions. A 20% increase in the Young's modulus of overhead ACSR lines has been measured over a period of 10 years. Since this has direct implications for line sag, monitoring Young's modulus is an excellent method to predict line sag problems that combine permanent annealing effects with transient thermal effects.

One advantage of the present invention is that the temperature is measured within the interior of the conductor, rather than at the surface of the conductor.

Another advantage of the present invention is that the conductor length can be measured using the same apparatus.

Another advantage of the present invention is that the sag of an overhead power line conductor can be calculated based on the measured conductor length.

Another advantage of the present invention is that it can be retrofitted to installed overhead power lines, transformer windings and underground coaxial power cables.

Another advantage of the present invention is that it requires low power to operate.

Another advantage of the present invention is that it is lightweight compared with other solutions.

Another advantage of the present invention is that it requires very few modeling parameters to give accurate measurements.

DETAILED DESCRIPTION OF THE PREFERRED EMBODIMENTS

Figure 1:
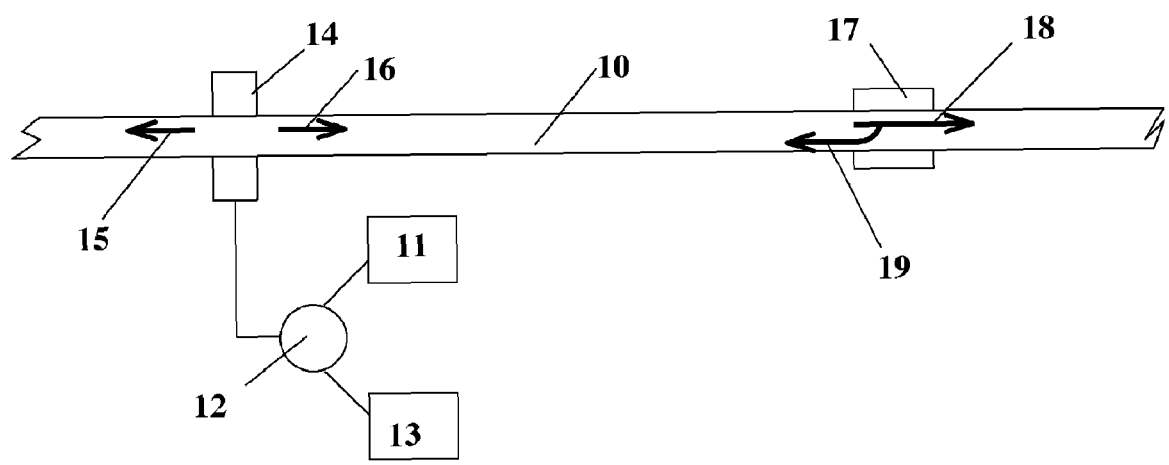
FIG. 1 is a schematic diagram of the sensor applied to an overhead conductor.

A thin cylindrical rod can support longitudinal (extension or bar) and transverse (torsional or shear) acoustic modes, along with a multitude of surface modes and combinations of modes. By controlling launch conditions and frequency content of the excitation, a subset of these modes can be excited.

The launch conditions, rod diameter and acoustic frequency all depend on the cable dimensions and the properties of the cable materials. For the present application, longitudinal or torsional waves are of primary interest. Such waves will propagate in both the core and sheath of a conductor. The solution of the wave equation for the cylindrical bar is quite tedious and is not presented here for the sake of brevity, but the results are directly analogous to those for both electromagnetic and fiber optic waveguides. The critical aspects of the solution are the cutoff frequency and velocity dispersion behavior for various possible modes. This data is typically presented in terms of phase velocity dispersion curves that plot the phase velocity for possible modes against the product of frequency f and diameter d of the rod. The larger the f*d product, known as the mode parameter, the larger the allowed number of acoustic modes.

When a single-frequency burst is used to excite longitudinal waves in a cylindrical conductor, the resulting sinc function spectrum is centered at the carrier frequency. If the mode parameter is sufficiently large, some portions of the burst spectrum may be cut off and others will travel at different velocities. This dispersion will result in a significantly different signature for the detected signal, which will complicate interpretation of the results. However, this problem can be minimized by selecting a sufficiently low frequency band for the given conductor diameter. In addition, to maximize the interaction of the acoustic wave with the conductor cross-section, the majority of the displacement energy should propagate in the conductor's interior. This is achieved by using low acoustic frequencies, since higher frequencies propagate closer to the conductor surface, and become Rayleigh waves at sufficiently high frequencies.

For example, in the case of aluminum, a frequency-diameter product of less than 2 MHz-mm ensures operation below the cutoff for all modes except the zero-order longitudinal mode. The zero-mode velocity dispersion curve is nearly flat in this regime, being approximately given by $c_{bar}(f)=\{Y_o/p*[1-(3.14*s*f*d/(2*c_{bar})^2)]\}^{0.5}$, where f is the acoustic frequency, s is Poisson's ratio, $Y_o$ is Young's modulus of the conductor, p is mass density of the bar, d is the bar diameter and $C_{bar}$ is the acoustic, or bar velocity based on strength-of-materials arguments. For a small mode parameter, the wave propagation velocity for all spectral components will be very close to the bar velocity given as $c_{bar}=\{Y_o/p\}^{0.5}$. In this case, the launched burst will suffer very little dispersion and the acoustic velocity is directly related to the modulus of the conductor.

Table I lists relevant acoustic properties of the materials found in an overhead cable, transformer winding or underground cable.

TABLE I

Acoustic properties of relevant materials.

| Property | Al | 347 SS | Cu | Pyrex | Polyethylene |
|---|---|---|---|---|---|
| Young's modulus $Y_o$ (GPa) | 70 | 196 | 125 | 62 | 0.76 |
| Lame constant μ (GPa) | 25 | 75.7 | 46 | 25 | 0.26 |
| Lame constant λ (GPa) | 61 | 113 | 131 | 23 | 2.88 |
| Poisson's Ratio, s | 0.355 | 0.30 | 0.37 | 0.24 | 0.458 |
| Mass density p(kg/m³) | 2699 | 7870 | 8930 | 2320 | 900 |
| Long. velocity (m/sec) | 6420 | 5790 | 5010 | 5640 | 1950 |
| Shear/Torsional wave velocity (m/sec) | 3040 | 3100 | 2270 | 3280 | 540 |
| Bar velocity (m/sec) | 5000 | 5000 | 3750 | 5170 | 920 |
| Longitudinal wave Impedance $Z_L$ (Mrayls) | 17.3 | 45.7 | 44.6 | 13.1 | 1.75 |
| Shear wave Impedance $Z_S$ (Mrayls) | 8.2 | 24.5 | 20.2 | 7.6 | 0.48 |
| CTE a (ppm/° C.) | 23.9 | 11.7 | 16.5 | 5 | 83-167 |
| Acoustic loss A (nepers/m-Hz²) | $2.3 \times 10^{-16}$ | $0.2 \times 10^{-16}$ | $4.5 \times 10^{-16}$ | $2.6 \times 10^{-22}$ | — |
| Long. Q, 10 kHz | — | 5000 | 300 | 170 | — |
| Torsional Q, 10 kHz | — | 32700 | 3000 | 775 | — |
| Loss (dB/km), 10 kHz | — | 5.2 | 120 | 156 | — |

Operation at lower frequencies is also important to minimize attenuation of the acoustic signal over long distances. Few studies have investigated the acoustic loss in thin cylindrical rods composed of stranded or heterogeneous materials. A lower limit can be estimated by looking at some of the fundamental loss mechanisms found in solids. Acoustic loss due to heat flow results from the rarefaction and compression of the solid, which heats or cools the body. The loss is proportional to the square of the acoustic frequency. This accounts for about half of the total thermal losses in single-grain metals. Typical values for this loss are given in Table I, and are extremely small.

Acoustic loss due to inter-grain heat flow is inversely proportional to the acoustic frequency above a relaxation frequency, which for metals is <100 kHz. Below the relaxation frequency, the loss is frequency independent.

Acoustic loss due to grain scattering has a direct analogy to Rayleigh scattering in electromagnetic theory. For frequencies well below the grain scattering resonant frequency, the loss varies as the fourth power of acoustic frequency.

A lower limit on acoustic losses can be estimated by doubling the acoustic losses due to heat flow given in Table I. For a steel core power cable with a length of 50 kilometers and an acoustic frequency of 10 kHz, the total loss is 0.0008 dB. Clearly, other loss mechanisms will increase this value considerably. Torsional waves usually have a factor-of-3 (or more) lower attenuation than longitudinal waves. The lowest loss material in this table, annealed steel, gives an attenuation of 5.2 dB/km for 10 kHz longitudinal waves, and 1.5 dB/km for 10 kHz torsional waves.

The transit time for an acoustic wave in a cable with bar velocity $V_E$ and length L is given by $\tau=L/V_E$, with a temperature dependence of $1/t\ dt/dT = a - 1/(2Y_o)dY_o/dT + 1/(2p)dp/dT$, where t is the transit time, p is the mass density and a is the linear thermal expansion coefficient, or CTE. The temperature dependence of Young's modulus $Y_o$ will provide the largest temperature dependent effect in the measured transit time of an acoustic tone burst. Typical data for polycrystalline Aluminum indicates a temperature dependence of <−100 ppm/C from −50 to +100 C, increasing to −570 ppm/C from 100-200 C. Steel has a Young's modulus temperature dependence of −450 ppm/C from −50 to +100 C, and −510 ppm/C from 100-200 C. Similar behavior is expected for copper. This is more than an order of magnitude larger than the length change induced by thermal expansion, of +12 ppm/C for steel and +23 ppm/C for Aluminum. The transit time can then be related to temperature and/or the cable length using one or more of several methods described below.

FIG. 1 is a schematic diagram of the disclosed method applied to an overhead power line. An overhead conductor 10 has an acoustic transducer 14 clamped on to allow acoustic energy to flow into or out of the conductor. The acoustic transducer 14 is electrically interfaced to a Transmit/Receive (T/R) switch 12, a waveform generator 11 and a digitizing data collection and analysis system 13. When the waveform generator 11 energizes the transducer 14, two acoustic waves 15 and 16 propagate away from the transducer 14 in opposite directions inside the conductor 10. The acoustic wave 16 eventually interacts with an acoustic perturbation 17 introduced onto the conductor, such as a cable clamp, a splice, a crimp, a termination or a sharp bend. The perturbation 17 causes a portion of the acoustic wave 16 to be reflected, resulting in two acoustic waves 19 and 18 traveling back to the transducer or continuing to travel away from the transducer, respectively. The acoustic wave 19 that is reflected from the perturbation 17 is detected by the transducer 14 and collected by the system 13. By measuring the transit time between the launched acoustic wave 16 start time and the detection time of acoustic reflection 19, the distance between the transducer 14 and perturbation 17 can be found, and/or the temperature of the conductor between transducer 14 and perturbation 17 can be found.

Figure 2:
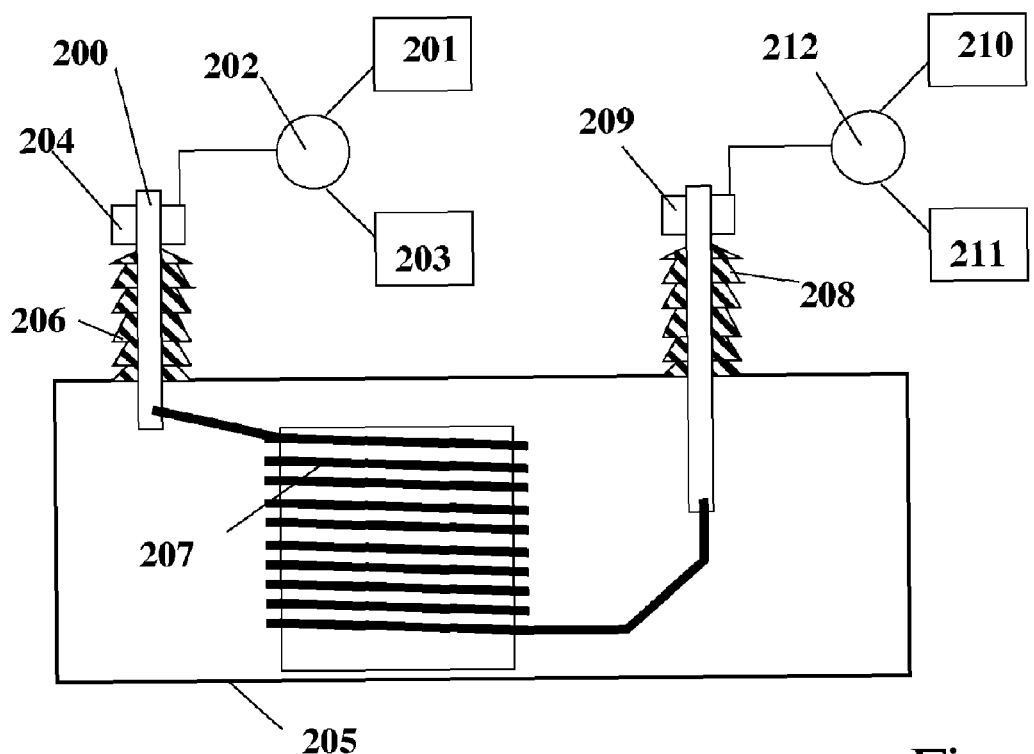
FIG. 2 is a schematic diagram of the sensor applied to the windings of a power transformer.

FIG. 2 is a schematic diagram of the disclosed method applied to measuring the temperature of a power transformer winding. The waveform generator 201, receiver 203, T/R switch 202 and transducer 204 are attached to the high voltage conductor 200 and bushing 206 of a power transformer 205. The bushing conductor 200 connects to one side of the transformer winding 207. The other end of the winding 207 is connected to a second bushing conductor 208. An acoustic wave is launched into the conductor 200 by the transducer 204 and propagates along the winding 207. At regular intervals, the conductor 200 undergoes sharp turns or experiences clamping points as part of the winding 207, resulting in a plurality of small acoustic reflections returning to the transducer 204. By measuring the return time of each reflection in the winding, the winding temperature can be determined. By measuring the return time difference between adjacent returning acoustic reflections, the temperature of the segment of conductor winding located between the two conductor bends causing the acoustic reflections can be calculated. By combining a plurality of measurements from the various reflections detected by the receiver 203, a temperature distribution of the transformer winding 207 can be determined. For windings that cause a large acoustic loss due to their shape or length, a second transducer 209 can be attached to the second bushing conductor 208. The transducer 209 is connected to T/R switch 212, waveform generator 210 and receiver 211. Reflections from the acoustic wave generated by transducer 209 can be used to calculate the temperature in the lower half of winding 207, whereas the temperature distribution in the upper half of winding 207 can be calculated using measurements from transducer 204. Alternatively, the signal generated by transducer 204 can be detected by transducer 209 to calculate the average temperature of the entire transformer winding 207.

Figure 3:
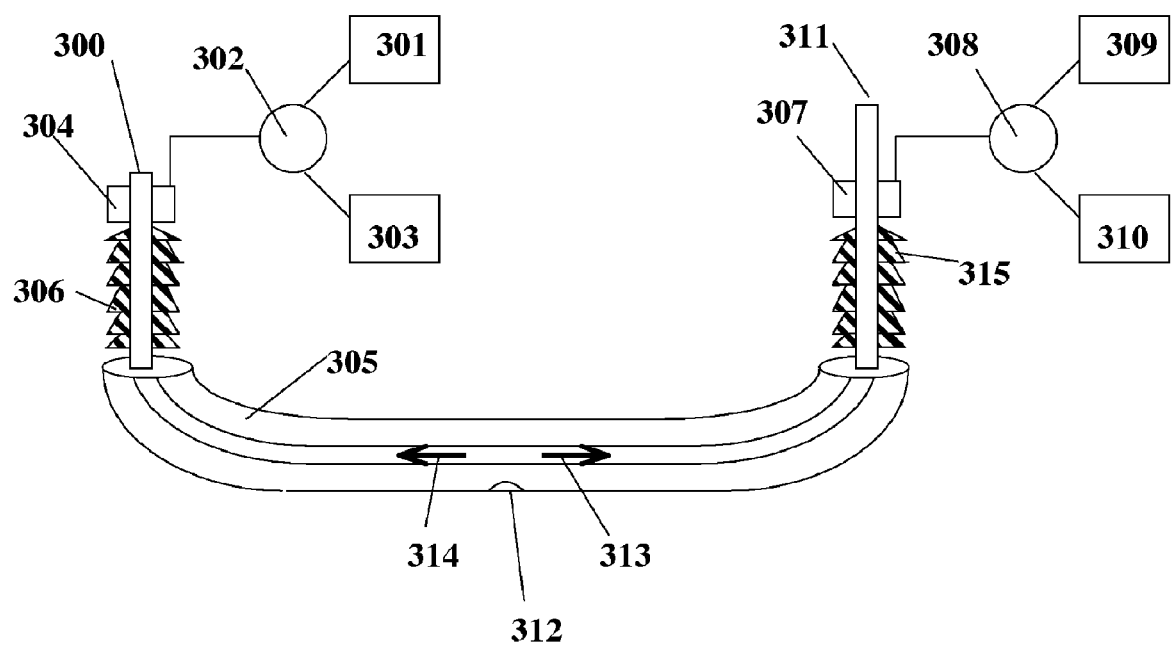
FIG. 3 is a schematic diagram of the sensor applied to an underground power cable.

FIG. 3 is a schematic diagram of the disclosed method applied to an underground or underwater coaxial power cable. The transducer 304 is connected to T/R switch 302, waveform generator 301 and receiver 303. The transducer is clamped to conductor 300 that is part of transition bushing 306 that provides a dielectric transition for the conductor 300 from the open air into the cable 305. The opposite end of the cable is terminated in a transition bushing 306. An acoustic wave 313 is coupled into conductor 300 by transducer 304 and propagates along the central conductor of cable 305. Sharp bends or distortions 312 in the cable cause acoustic reflections 314 that return to transducer 304 where they are detected and recorded by receiver 303. The time delay between the start of acoustic wave 313 and the detection of reflection 314 can be used to calculate the distance from the transducer 304 to the distortion 312. Alternatively, the time delay can be used to calculate the temperature of the cable between the transducer 304 and the distortion 312. The acoustic wave 313 eventually reaches the opposite end of the cable 305, where it is reflected by the termination 311. The reflected wave travels back to transducer 304 where it is detected. The time delay between this reflected wave and the start of the acoustic wave 313 is used to calculate the average temperature of the central conductor of the cable 305. The acoustic wave 313 can also be detected and recorded by a second transducer 307, T/R switch 308, waveform generator 309 and receiver 310, where the transducer 307 is clamped to the second transition bushing 315.

A number of approaches are now disclosed regarding the choice of acoustic wave and the required signal processing that may be applied to any of the applications already described above and shown in FIGS. 1, 2 and 3. In the descriptions that follow, the T/R switch, waveform generator and receiver are not shown, but are assumed to be present.

Figure 4:
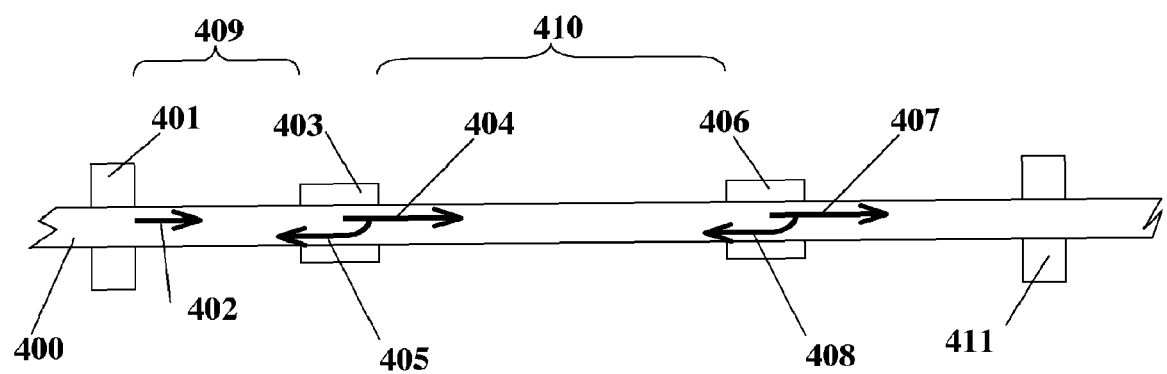
FIG. 4 is a schematic diagram of a first embodiment of the sensor.

A first approach, shown in FIG. 4, consists of a transducer 401 clamped to a conductor 400 that generates an acoustic wave 402. A clamp or other device 406 is attached to the conductor 400 a known, short distance from the transducer. The time of flight of the first reflection 405 returned to the transducer is used to determine the temperature of the conductor, since the length of conductor between the transducer and the clamp is known. The time delay is proportional to the group velocity of the acoustic wave 402 and 405, which in turn has known temperature dependence for the material from which the conductor 400 is fabricated. The majority of the acoustic wave 402 continues past the clamp 403 as acoustic wave 404 with slightly diminished amplitude. A subsequent reflection 408 generated by a second defect or clamp 406 further along the cable is used to provide a second time of flight. In addition, the time delay between the arrival of the first reflection 405 and the second reflection 408 can be used to determine the temperature or length of the second section of conductor. If the first section of conductor 409 is much shorter than the second section of conductor 410, then the time delay between reflections 405 and 408 is mainly controlled by the second section of conductor 410. The first reflection time delay 405 can be used to calculate the temperature of the conductor. Assuming that the temperature along the cable is constant, then the difference time delay between reflections 405 and 408 can be used to calculate the length of the long section of conductor 410. With knowledge of the fixed support locations of the conductor in an overhead line application, the conductor sag can then be computed. A second transducer 411 attached to the conductor 400 a known distance from the first transducer 400 can alternatively be used to detect the transmitted acoustic wave 407. The time delay between the detection of wave 407 at transducer 411 and the start of wave 402 at transducer 401 can be used to determine the average temperature of the conductor sections 409 and 410. By combining this time delay with a measurement of the temperature of the conductor section 409, the length of conductor sections 409 and 410 can be calculated, and in an overhead line application, the conductor sag can be estimated.

Figure 5:
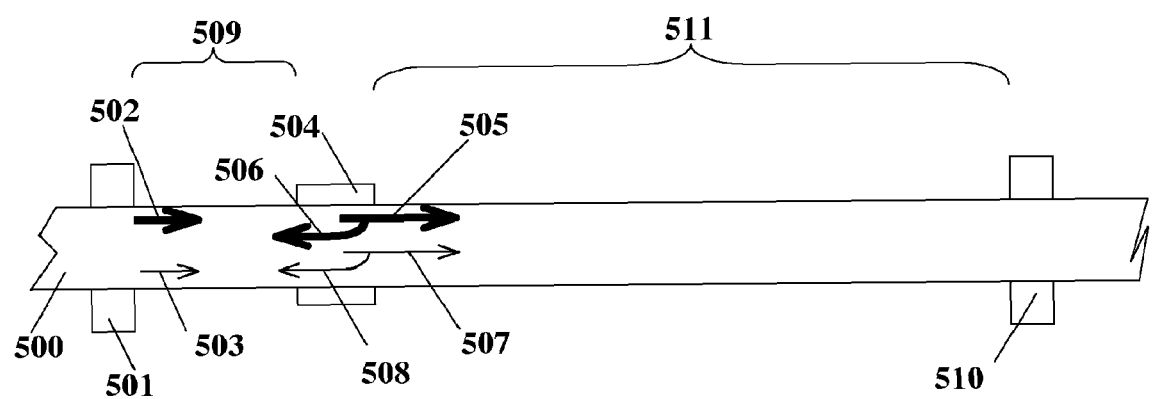
FIG. 5 is a schematic diagram of a second embodiment of the sensor.

A second approach is shown in FIG. 5. A conductor 500 has a transducer 501 clamped to it. The transducer has the ability to launch and receive both a longitudinal acoustic wave 502 and a torsional acoustic wave 503 along the conductor 500. Both waves 502 and 503 have the same frequency but they travel at different group velocities and they have different group velocity temperature dependencies. A clamp or other device 504 is attached to the conductor 500 some distance from the transducer. The two waves 502 and 503 arrive at the clamp 504 at different times, and a portion of each wave is reflected back towards the transducer 501 as waves 506 and 508, respectively. The two acoustic waves 506 and 508 are detected by transducer 500. The time delay between receiving the two waves can be used to calculate the length of the conductor and the temperature of the conductor section 509. The remaining waves 505 and 507 continue along the conductor and can be detected by a second transducer 510 that is capable of detecting both longitudinal and torsional waves. The time delay between the arrival of the two waves 505 and 507 can be used to determine the temperature and length of the conductor sections 509 and 511. The time delay is proportional to the group velocity of the acoustic wave 502 or 503, which in turn has known temperature dependence for the material from which the conductor 500 is fabricated. With knowledge of the fixed support locations of the conductor in an overhead line application, the conductor sag can then be computed.

Figure 6:
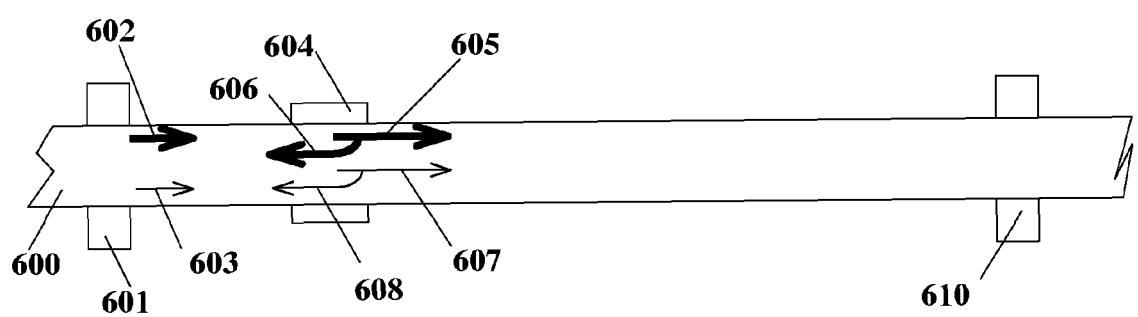
FIG. 6 is a schematic diagram of a third embodiment of the sensor.

A third approach, shown in FIG. 6, has a transducer 601 clamped to a conductor 600. The transducer 601 generates two longitudinal or torsional acoustic waves 602 and 603 having different center frequencies. One acoustic wave 602 with a lower center frequency is selected to propagate along the conductor as a lowest order mode with a first group velocity. The second acoustic wave 603 with a higher center frequency is selected to propagate along the conductor in a higher order mode with a second group velocity. The two waves also have different temperature coefficients of velocity. The two acoustic waves can generate reflections 606 and 608 at a clamp 604, or the remaining acoustic waves 605 and 607 can continue on to a second transducer 610. The difference in arrival time between the two acoustic waves arriving at transducer 601 or 610 can be used to determine the temperature of the conductor and the length of the conductor section being tested. With knowledge of the fixed support locations of the conductor in an overhead line application, the conductor sag can then be computed.

Figure 7:
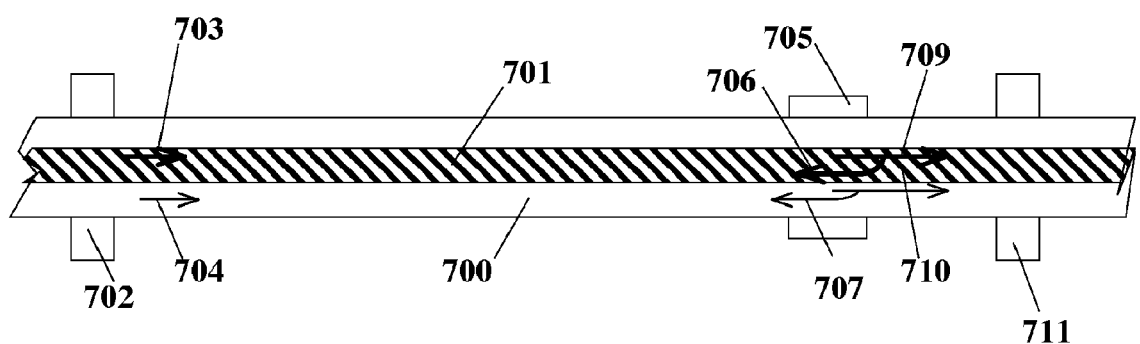
FIG. 7 is a schematic diagram of a fourth embodiment of the sensor.

In a fourth approach, shown in FIG. 7, a transducer 702 is clamped to a conductor composed of an inner core 701 (such as steel) and an outer cladding 700 (such as aluminum). The transducer 702 launches a longitudinal or torsional wave into the conductor, where a portion of the wave travels in the conductor core 701 as wave 703, and the remainder of the wave energy travels in the cladding 700 as wave 704. The launched waves 703 and 704 travel in the two cable regions at different velocities, and experience different temperature dependencies of their velocities. For example, a commonly used overhead power line conductor consists of a steel core surrounded by an aluminum cladding. In the temperature range of −50 to +100 C, the Young's modulus of Aluminum is almost independent of temperature, whereas the Young's modulus of the steel core varies by −450 ppm/C. Therefore, the velocity in aluminum is almost unchanged over this temperature range, whereas it varies considerably in steel. The two acoustic waves can generate reflections 706 and 707 at a clamp 705, or the remaining acoustic waves 709 and 710 can continue on to a second transducer 711. The difference in arrival time between the two acoustic waves arriving at transducer 702 or 711 can be used to determine the temperature of the conductor and the length of the conductor section being tested. With knowledge of the fixed support locations of the conductor in an overhead line application, the conductor sag can then be computed.

Figure 8:
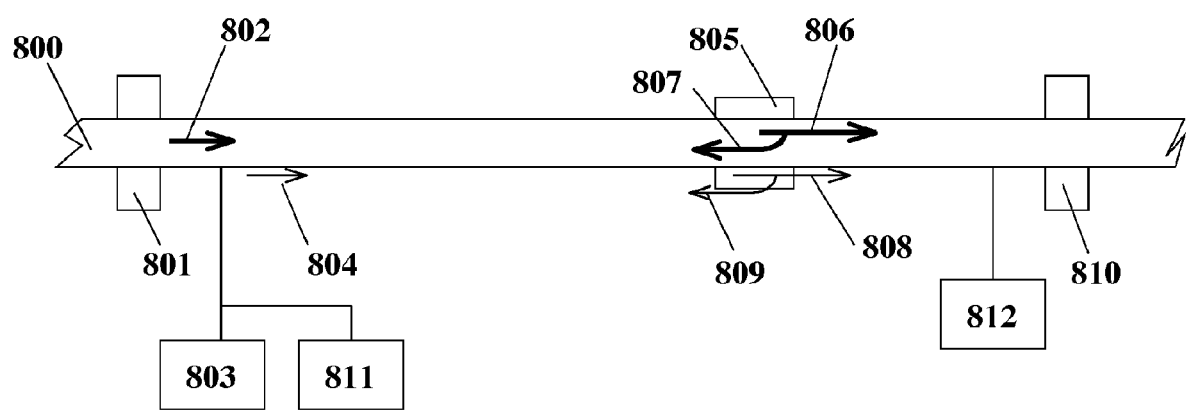
FIG. 8 is a schematic diagram of a fifth embodiment of the sensor.

In a fifth approach, shown in FIG. 8, an electromagnetic pulse 804 is launched by a pulse generator 803 along the conductor 800 at the same time that a longitudinal or torsional acoustic wave 802 is launched by transducer 801. The electromagnetic pulse reflects from a clamp or other perturbation 805 along the conductor. The resulting reflected electromagnetic pulse 807 is detected by electronic detector 811 and its arrival time is measured relative to the launch time of pulse 804. The group velocity of the electromagnetic pulse is substantially independent of the conductor temperature. The total elapsed travel time of the electromagnetic pulse is used to determine the distance or range from the generator 803 to the clamp or perturbation 805. The time of flight of the reflected acoustic wave 809 is also measured relative to the start time of the acoustic wave 802. The acoustic wave travel time is used to calculate the temperature of the conductor 800 along its length. The remaining electromagnetic pulse 806 and acoustic wave 808 can also be detected by a second transducer 810 and a second electronic receiver 812. The Time of flight of the electromagnetic pulse is used to calculate the length of the conductor section, and the time of flight of the acoustic wave is used to calculate the temperature of the conductor section.

Figure 9:
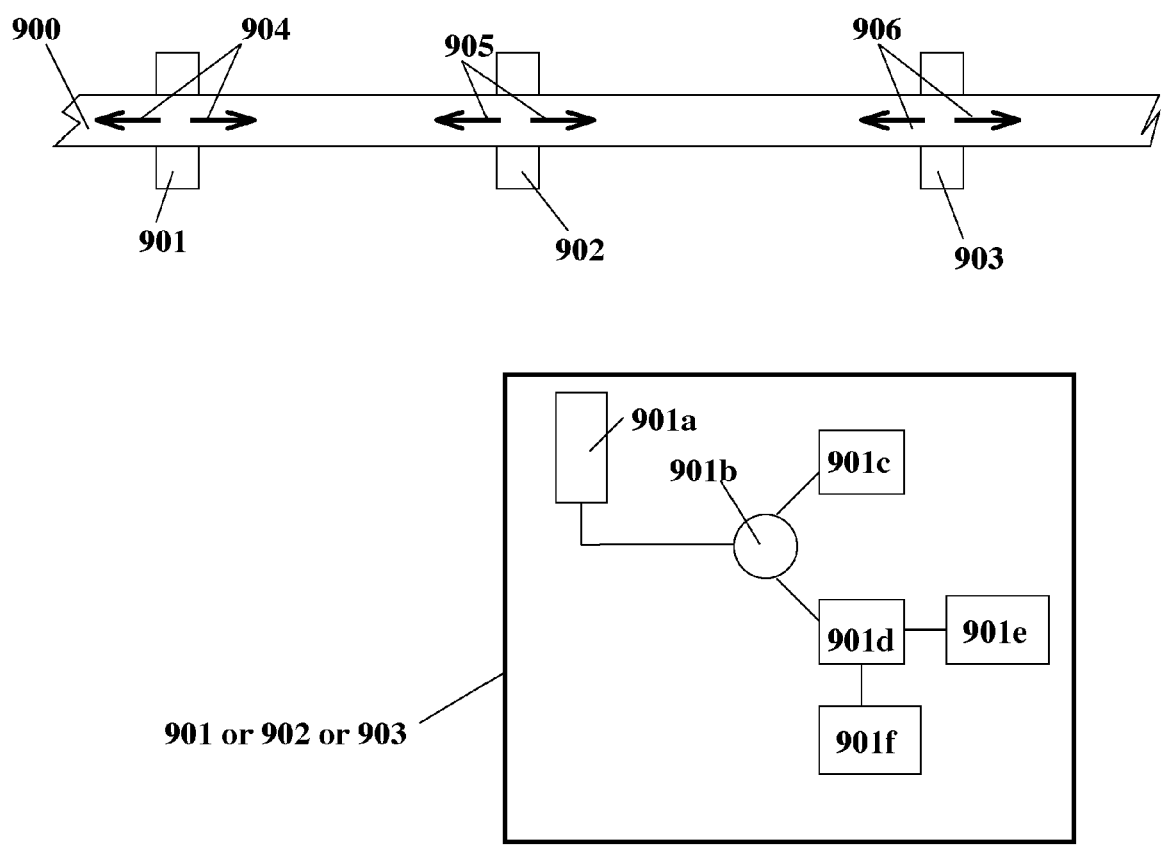
FIG. 9 is a schematic diagram of a sixth embodiment of the sensor.

A sixth approach uses a plurality of transducers along the conductor. As shown in FIG. 9, a transponder 901, 902 or 903 is comprised of a transducer 901*a*, a T/R switch 901*b*, a waveform generator 901*c*, a receiver 901*d*, a real time clock 901*e* and a data storage unit 901*f*. Each transponder 901, 902 and 903 (three transponders are shown for illustrative purposes, although the number can be much larger than this) generates an acoustic wave 904, 905 and 906 that is encoded with the transponder identification and the absolute time that the acoustic wave was launched. Each transponder also receives the acoustic waves launched by the other transponders clamped to the conductor. For example, transponder 902 receives acoustic wave 904 generated by transponder 901, and acoustic wave 906 generated by transponder 903. The acoustic waves received by each transponder are decoded and the transponder identification and the time delay associated with that acoustic wave are stored in each transponder 901, 902 or 903. Each transponder also includes a reference clock that is used to determine the time of flight for each detected acoustic wave. This is accomplished by recording the time that an acoustic wave is received, decoding the start time that is coded into the acoustic wave, and digitally subtracting these two times to arrive at a travel time for the acoustic wave. A database is included in each transponder 901, 902 or 903 that is comprised of the time delay for travel between a transponder and every other transponder clamped to the conductor. The resulting database stored in the transponders can be used to determine temperature and conductor length in each section separating two transponders.

The launch transducer should be capable of introducing longitudinal waves and/or torsional waves into the conductor. In addition, the transducer must be able to clamp onto a conductor, and be capable of operating reliably over an extended temperature range (−40 to +150 C). Piezoelectric (such as Lead Zirconate Titanate ceramics), electromagnetic (EMAT) and magneto-acoustic (based on Terfenol-D) drivers are all candidate technologies for this application. However, piezoelectric ceramic transducers provide a good combination of low cost, availability, reasonably high mechanical stiffness and good efficiency.

For all of the measurement methods described, the time of flight can be measured in a number of ways. The simplest method involves using a comparator to determine when the detected acoustic signal exceeds a threshold level. A second method uses a tone burst that is coded, for example by amplitude modulating each cycle of the burst to impart information about the origin of the burst. This data can be detected using commonly available technologies such as code division multiple access (CDMA) or a Universal Asynchronous Receiver Transmitter (UART). A third method uses a ring-around technique, whereby the detection of an acoustic wave triggers the launching of a second acoustic wave. This process repeats indefinitely. The travel time can be inferred by measuring the repetition rate of the launched acoustic wave. This method can be very precise since it provides averaging of variations in each individual round trip time, and the frequency can be very precisely measured (to better than 1 ppm).

While particular embodiments of the present invention have been illustrated and described, it is understood that the invention is not limited to the precise construction and compositions disclosed herein and that various modifications, changes, and variations will be apparent that lie within the scope and spirit of the invention as defined in the attached claims.

What is claimed is:

1. A temperature sensor and extensometer for monitoring an electrical conductor, comprised of one or more acoustic generators attached along said conductor where the said acoustic generators emit one or more acoustic signals consisting of a sinusoid of finite extent in time and having a narrow range of acoustic frequencies, where the said acoustic signals travel in the said conductor as longitudinal or torsional acoustic waves, where the frequency of said acoustic signals are selected to ensure that the acoustic signals are launched in said conductor as both the lowest order longitudinal acoustic wave and the lowest order torsional acoustic wave, where one or more acoustic detectors are attached along said conductor, where an electronic timer measures the time between the launching of one or more said acoustic signals by said acoustic generators and the detection of one or more said acoustic signals by said acoustic detectors, where the signal processor computes the travel time of a first acoustic signal between two locations on said conductor where the travel time has a first temperature dependence, and computes the travel time of a second acoustic signal between two locations on said conductor where the travel time has a second temperature dependence, such that the difference or ratio of travel times can be used to calculate the temperature along the region of said conductor wherein the acoustic signals traveled, where the travel times can be used to calculate the distance traveled by the acoustic signals, and where said conductor is embedded in an electrical apparatus including but not limited to a power transformer.

2. The sensor in claim 1 where one or more sensors are attached to one or more conductors located at the exterior of a power transformer.

3. The sensor in claim 1 where the acoustic signals are modulated in each successive emission of the acoustic signals, where information is modulated onto said acoustic signals using one or more of the methods including but not limited to amplitude or phase modulation, and where the information may include but is not limited to the absolute time the said acoustic signals were generated, the identification of the said acoustic generator, the identification of the intended acoustic detector of the said acoustic signals, the physical location of the intended acoustic detector of the said acoustic signals, the intended absolute time prior to which the intended acoustic detector must receive the said acoustic signals, the intended absolute time after which the intended acoustic detector must receive the said acoustic signals, or the physical location of the said acoustic generator.

4. A temperature sensor and extensometer for monitoring an electrical conductor, comprised of one or more acoustic generators attached along said conductor where the said acoustic generators emit one or more acoustic signals consisting of a sinusoid of finite extent in time and having a narrow range of acoustic frequencies, where the said acoustic signals travel in the said conductor as longitudinal or torsional acoustic waves, where the frequency of said acoustic signals are selected to ensure that the acoustic signals are launched in said conductor as a superposition of the lowest order and first order longitudinal acoustic waves in the said conductor, where one or more acoustic detectors are attached along said conductor, where an electronic timer measures the time between the launching of one or more said acoustic signals by said acoustic generators and the detection of one or more said acoustic signals by said acoustic detectors, where the signal processor computes the travel time of a first acoustic signal between two locations on said conductor where the travel time has a first temperature dependence, and computes the travel time of a second acoustic signal between two locations on said conductor where the travel time has a second temperature dependence, such that the difference or ratio of travel times can be used to calculate the temperature along the region of said conductor wherein the acoustic signals traveled, where the travel times can be used to calculate the distance traveled by the acoustic signals, and where said conductor is embedded in an electrical apparatus including but not limited to a power transformer.

5. The sensor in claim 4 where one or more sensors are attached to one or more conductors located at the exterior of a power transformer.

6. The sensor in claim 4 where the acoustic signals are modulated in each successive emission of the acoustic signals, where information is modulated onto said acoustic signals using one or more of the methods including but not limited to amplitude or phase modulation, and where the information may include but is not limited to the absolute time the said acoustic signals were generated, the identification of the said acoustic generator, the identification of the intended acoustic detector of the said acoustic signals, the physical location of the intended acoustic detector of the said acoustic signals, the intended absolute time prior to which the intended acoustic detector must receive the said acoustic signals, the intended absolute time after which the intended acoustic detector must receive the said acoustic signals, or the physical location of the said acoustic generator.

7. A temperature sensor and extensometer for monitoring an electrical conductor, comprised of one or more acoustic generators attached along said conductor where the said acoustic generators emit one or more acoustic signals consisting of a sinusoid of finite extent in time and having a narrow range of acoustic frequencies, where the said acoustic signals travel in the said conductor as longitudinal or torsional acoustic waves, where the frequency of said acoustic signals are selected to ensure that the acoustic signals are launched in said conductor as a superposition of the lowest order and first order torsional acoustic waves in the said conductor, where one or more acoustic detectors are attached along said conductor, where an electronic timer measures the time between the launching of one or more said acoustic signals by said acoustic generators and the detection of one or more said acoustic signals by said acoustic detectors, where the signal processor computes the travel time of a first acoustic signal between two locations on said conductor where the travel time has a first temperature dependence, and computes the travel time of a second acoustic signal between two locations on said conductor where the travel time has a second temperature dependence, such that the difference or ratio of travel times can be used to calculate the temperature along the region of said conductor wherein the acoustic signals traveled, where the travel times can be used to calculate the distance traveled by the acoustic signals, and where said conductor is embedded in an electrical apparatus including but not limited to a power transformer.

8. The sensor in claim 7 where one or more sensors are attached to one or more conductors located at the exterior of a power transformer.

9. The sensor in claim 7 where the acoustic signals are modulated in each successive emission of the acoustic signals, where information is modulated onto said acoustic signals using one or more of the methods including but not limited to amplitude or phase modulation, and where the information may include but is not limited to the absolute time the said acoustic signals were generated, the identification of the said acoustic generator, the identification of the intended acoustic detector of the said acoustic signals, the physical location of the intended acoustic detector of the said acoustic signals, the intended absolute time prior to which the intended acoustic detector must receive the said acoustic signals, the intended absolute time after which the intended acoustic detector must receive the said acoustic signals, or the physical location of the said acoustic generator.

10. A temperature sensor and extensometer for monitoring an electrical conductor, comprised of one or more acoustic generators attached along said conductor where the said acoustic generators emit one or more acoustic signals consisting of a sinusoid of finite extent in time and having a narrow range of acoustic frequencies, where the said acoustic signals travel in the said conductor as longitudinal or torsional acoustic waves, where the frequency of said acoustic signals are selected to ensure that the acoustic signals are comprised of a first frequency of sufficiently low value that it propagates in the conductor as the lowest order longitudinal acoustic wave or torsional acoustic wave, and a second frequency having such a value that it propagates as a superposition of the lowest order and first order longitudinal acoustic modes or torsional acoustic modes in the said conductor, where one or more acoustic detectors are attached along said conductor, where an electronic timer measures the time between the launching of one or more said acoustic signals by said acoustic generators and the detection of one or more said acoustic signals by said acoustic detectors, where the signal processor computes the travel time of a first acoustic signal between two locations on said conductor where the travel time has a first temperature dependence, and computes the travel time of a second acoustic signal between two locations on said conductor where the travel time has a second temperature dependence, such that the difference or ratio of travel times can be used to calculate the temperature along the region of said conductor wherein the acoustic signals traveled, where the travel times can be used to calculate the distance traveled by the acoustic signals, and where said conductor is embedded in an electrical apparatus including but not limited to a power transformer.

11. The sensor in claim 10 where one or more sensors are attached to one or more conductors located at the exterior of a power transformer.

12. The sensor in claim 10 where the acoustic signals are modulated in each successive emission of the acoustic signals, where information is modulated onto said acoustic signals using one or more of the methods including but not limited to amplitude or phase modulation, and where the information may include but is not limited to the absolute time the said acoustic signals were generated, the identification of the said acoustic generator, the identification of the intended acoustic detector of the said acoustic signals, the physical location of the intended acoustic detector of the said acoustic signals, the intended absolute time prior to which the intended acoustic detector must receive the said acoustic signals, the intended absolute time after which the intended acoustic detector must receive the said acoustic signals, or the physical location of the said acoustic generator.

* * * * *